US010426470B2

(12) United States Patent
Guerrera

(10) Patent No.: US 10,426,470 B2
(45) Date of Patent: Oct. 1, 2019

(54) STAPLING DEVICE WITH RELEASABLE KNIFE CARRIER

(71) Applicant: Covidien LP, Mansfield, MA (US)

(72) Inventor: Joseph Guerrera, Watertown, CT (US)

(73) Assignee: Covidien LP, Mansfield, MA (US)

( * ) Notice: Subject to any disclaimer, the term of this patent is extended or adjusted under 35 U.S.C. 154(b) by 396 days.

(21) Appl. No.: 15/343,995

(22) Filed: Nov. 4, 2016

(65) Prior Publication Data

US 2018/0125486 A1 May 10, 2018

(51) Int. Cl.
*A61B 17/072* (2006.01)
*A61B 17/115* (2006.01)
*A61B 17/00* (2006.01)

(52) U.S. Cl.
CPC .... *A61B 17/07207* (2013.01); *A61B 17/1155* (2013.01); *A61B 2017/00398* (2013.01);
(Continued)

(58) Field of Classification Search
CPC ...... A61B 17/1155; A61B 2017/00477; A61B 2017/07214; A61B 2017/07271
See application file for complete search history.

(56) References Cited

U.S. PATENT DOCUMENTS 3,193,165 A  7/1965 Akhalaya et al.
3,388,847 A  6/1968 Kasulin et al.
(Continued)

FOREIGN PATENT DOCUMENTS

CA  908529 A  8/1972
CA  2805365 A1  8/2013
(Continued)

OTHER PUBLICATIONS

Extended European Search Report from Appl. No. 14181908.6 dated May 26, 2015.
(Continued)

*Primary Examiner* — Hemant Desai
*Assistant Examiner* — Veronica Martin

(57) ABSTRACT

A circular surgical stapling device includes a reload assembly that is supported on a distal end of an elongate shaft of the stapling device. The reload assembly includes a housing, a pusher assembly movably supported within the housing, a knife carrier movably supported within the pusher assembly, and an annular knife supported on the knife carrier. The elongate body includes a pusher drive member and a knife carrier pusher. The knife carrier includes first engagement structure that is configured to releasably engage second engagement structure formed on the knife carrier pusher to releasably couple the knife carrier pusher to the knife carrier. A reload insert or member is supported on or integrally formed with the housing of the reload assembly. The reload member includes a first portion configured to prevent separation of the first and second engagement structures and a second portion configured to accommodate separation of the first and second engagement structures. The reload member minimizes the likelihood of premature disengagement of the knife carrier from the knife carrier pusher while minimizing the force required to effect separation after the knife has been fully retracted into the housing.

20 Claims, 8 Drawing Sheets

(52) U.S. Cl.
CPC ........... *A61B 2017/00477* (2013.01); *A61B 2017/07228* (2013.01); *A61B 2017/07278* (2013.01); *A61B 2017/07285* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,250,058 A * | 10/1993 | Miller ............... A61B 17/11 24/615 |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,346,501 A * | 9/1994 | Regula ............... A61B 17/1114 606/151 |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |

(56) References Cited

U.S. PATENT DOCUMENTS

| | | |
|---|---|---|
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Vveisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |

(56) References Cited

U.S. PATENT DOCUMENTS

| | | | |
|---|---|---|---|
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 * | 7/2012 | Hessler ............... A61B 17/1114 227/179.1 |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 * | 10/2013 | Nalagatla ............ A61B 17/1114 227/175.1 |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,662,370 | B2 | 3/2014 | Takei |
| 8,663,258 | B2 | 3/2014 | Bettuchi et al. |
| 8,672,931 | B2 | 3/2014 | Goldboss et al. |
| 8,678,264 | B2 | 3/2014 | Racenet et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,733,611 | B2 | 5/2014 | Milliman |
| 9,038,882 | B2 * | 5/2015 | Racenet ............... A61B 17/072 227/180.1 |
| 9,351,724 | B2 * | 5/2016 | Penna ................. A61B 17/068 |
| 9,554,802 | B2 * | 1/2017 | Williams ............ A61B 17/1155 |
| 9,980,730 | B2 * | 5/2018 | Sgroi ................... A61B 17/068 |
| 10,039,549 | B2 * | 8/2018 | Williams ............ A61B 17/105 |
| 10,111,684 | B2 * | 10/2018 | Williams ............ A61B 17/115 |
| 2003/0111507 | A1 | 6/2003 | Nunez |
| 2004/0073090 | A1 | 4/2004 | Butler et al. |
| 2005/0051597 | A1 | 3/2005 | Toledano |
| 2005/0107813 | A1 | 5/2005 | Gilete Garcia |
| 2006/0000869 | A1 | 1/2006 | Fontayne |
| 2006/0011698 | A1 | 1/2006 | Okada et al. |
| 2006/0201989 | A1 | 9/2006 | Ojeda |
| 2007/0027473 | A1 | 2/2007 | Vresh et al. |
| 2007/0029363 | A1 | 2/2007 | Popov |
| 2007/0060952 | A1 | 3/2007 | Roby et al. |
| 2009/0236392 | A1 | 9/2009 | Cole et al. |
| 2009/0236398 | A1 | 9/2009 | Cole et al. |
| 2009/0236401 | A1 | 9/2009 | Cole et al. |
| 2010/0019016 | A1 | 1/2010 | Edoga et al. |
| 2010/0051668 | A1 | 3/2010 | Milliman et al. |
| 2010/0084453 | A1 | 4/2010 | Hu |
| 2010/0147923 | A1 | 6/2010 | D'Agostino et al. |
| 2010/0163598 | A1 | 7/2010 | Belzer |
| 2010/0224668 | A1 | 9/2010 | Fontayne et al. |
| 2010/0230465 | A1 | 9/2010 | Smith et al. |
| 2010/0258611 | A1 | 10/2010 | Smith et al. |
| 2010/0264195 | A1 | 10/2010 | Bettuchi |
| 2010/0327041 | A1 | 12/2010 | Milliman et al. |
| 2011/0011916 | A1 | 1/2011 | Levine |
| 2011/0114697 | A1 | 5/2011 | Baxter, III et al. |
| 2011/0114700 | A1 | 5/2011 | Baxter, III et al. |
| 2011/0144640 | A1 | 6/2011 | Heinrich et al. |
| 2011/0147432 | A1 | 6/2011 | Heinrich et al. |
| 2011/0192882 | A1 | 8/2011 | Hess et al. |
| 2012/0145755 | A1 | 6/2012 | Kahn |
| 2012/0193395 | A1 | 8/2012 | Pastorelli et al. |
| 2012/0193398 | A1 | 8/2012 | Williams et al. |

(56) References Cited

U.S. PATENT DOCUMENTS

| | | |
|---|---|---|
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1* | 5/2013 | Milliman .............. A61B 1/31 227/175.1 |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1* | 7/2013 | Olson ................ A61B 17/1155 227/180.1 |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1* | 8/2013 | Penna ................ A61B 17/115 227/179.1 |
| 2013/0214027 A1* | 8/2013 | Hessler .............. A61B 17/1114 227/175.1 |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0197225 A1* | 7/2014 | Penna ................ A61B 17/068 227/179.1 |
| 2016/0000428 A1* | 1/2016 | Scirica ............... A61B 50/30 227/180.1 |
| 2016/0361057 A1* | 12/2016 | Williams ............ A61B 17/068 |
| 2018/0125495 A1* | 5/2018 | Sgroi, Jr. ............ A61B 17/1155 |
| 2018/0233850 A1* | 8/2018 | Penna ................ H01R 13/5224 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |
| WO | 2016000247 A1 | 1/2016 |
| WO | 2016164519 A1 | 10/2016 |

OTHER PUBLICATIONS

European Examination Report from Appl. No. 14181908.6 dated May 3, 2016.

European Search Report dated Jan. 31, 2018, issued in EP Appln. No. 17199972.

European Office Action dated Dec. 14, 2018, issued in EP Appln. No. 17 199 972.

* cited by examiner

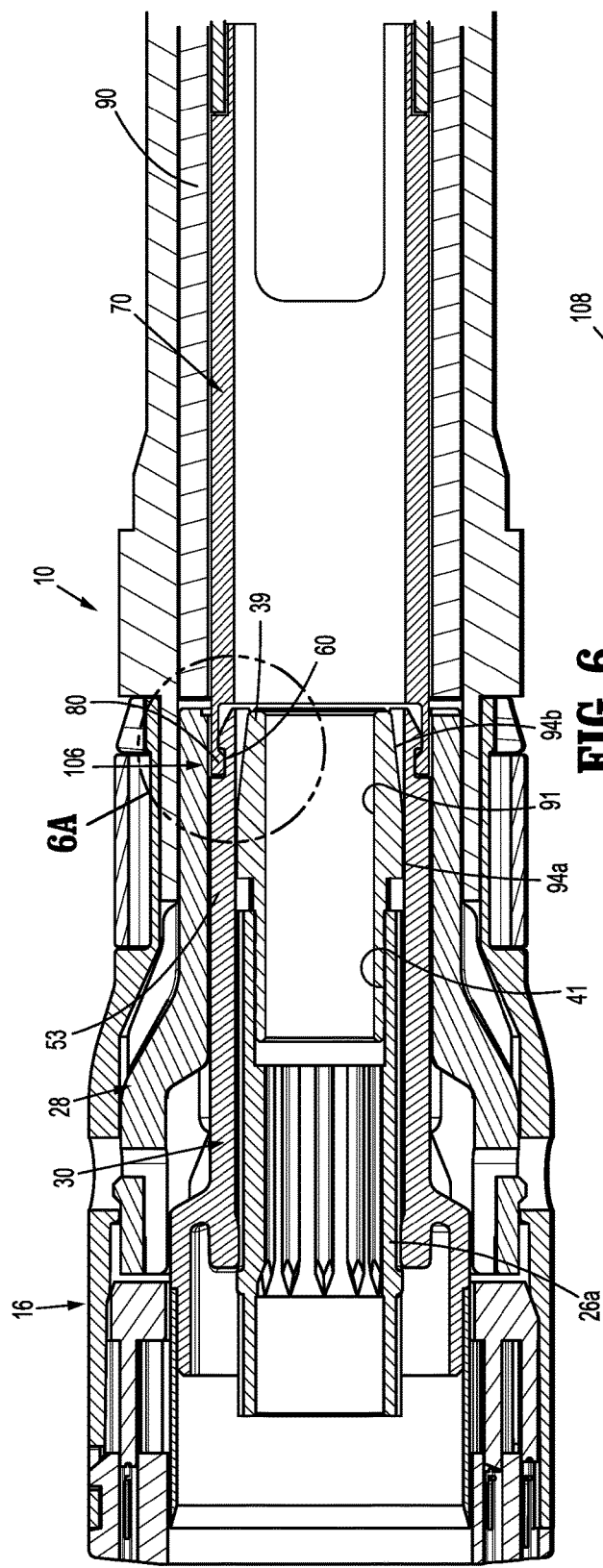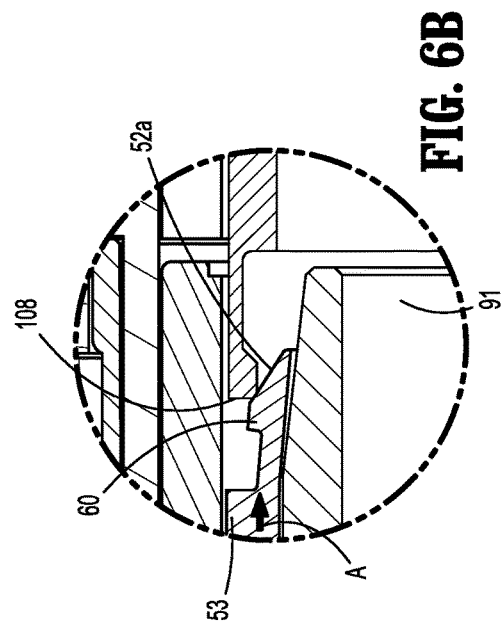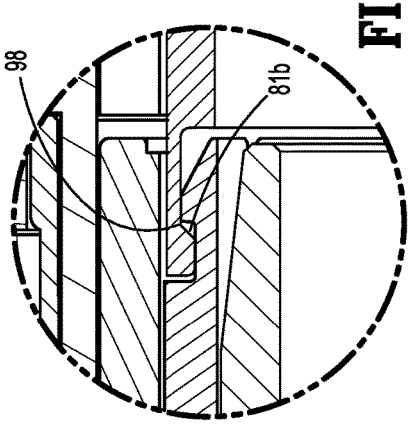

STAPLING DEVICE WITH RELEASABLE KNIFE CARRIER

BACKGROUND

1. Technical Description

The present disclosure is directed to circular stapling devices and, more particularly, to circular stapling devices that include a knife carrier that is releasably coupled to a knife carrier pusher.

2. Background of Related Art

Conventional circular stapling devices include an elongate body and a shell or reload assembly supported on a distal end of the elongate body. The reload assembly includes a staple cartridge that supports a plurality of staples, a pusher that is movable in relation to the staple cartridge to eject staples from the staple cartridge, a knife, and a knife carrier that supports the knife and is movable through the staple cartridge to core tissue. The surgical stapling device also includes a pusher drive member and a knife carrier pusher that are supported within the elongate body. The pusher drive member is engaged with the staple pusher and is movable to move the staple pusher to eject staples from the staple cartridge. Similarly, the knife carrier pusher is engaged with the knife carrier and is movable to effect movement of the knife carrier to core tissue. In some circular stapling devices, the knife carrier pusher and the knife carrier are separable to facilitate separation of the reload assembly from the elongate body of the surgical stapling device.

In current designs, a back angle is formed on the knife carrier pusher to facilitate separation of the knife carrier pusher from the knife carrier. In these designs, if the back angle selected is too small, the knife carrier can be damaged upon removal of the reload from the elongate body, and if the back angle selected is too large, disengagement of the knife carrier pusher from the knife carrier can occur prematurely such that full retraction of the knife is not achieved.

A need exists in the stapling arts for a simple but reliable mechanism to effect engagement and disengagement of the knife carrier and the knife carrier pusher at the appropriate times.

SUMMARY

In one aspect of the disclosure, a surgical stapling device includes an elongate body, a reload assembly, and a reload member. The elongate body defines a longitudinal axis and has a proximal portion and a distal portion. The elongate body includes a pusher drive member and a knife carrier pusher. The reload assembly includes a housing having an inner housing portion defining a housing through bore, a staple cartridge supporting a plurality of staples, a pusher assembly movably supported within the housing between a retracted position and an advanced position to eject the plurality of staples from the staple cartridge, and a knife carrier supporting a knife. The knife carrier includes a first engagement structure and the knife carrier pusher includes a second engagement structure that is configured to releasably engage the first engagement structure of the knife carrier to couple the knife carrier pusher to the knife carrier. The first engagement structure is movable from a first position engaged with the second engagement structure to a second position disengaged from the second engagement structure. The reload member is supported on the housing and has a first portion configured to prevent movement of the first engagement structure from the first position to the second position and a second portion configured to accommodate movement of the first engagement member from the first position to the second position.

In embodiments, the reload member includes an insert secured to the inner housing portion.

In some embodiments, the insert defines a through bore and includes a distal portion configured to be received within the housing through bore and a proximal portion that defines the first and second portions of the reload member.

In certain embodiments, the first portion of the reload member is cylindrical and the second portion of the reload member tapers from the first portion towards a longitudinal axis of the reload member in a proximal direction.

In embodiments, the knife carrier is movably positioned within a through bore defined by the pusher assembly.

In some embodiments, the knife carrier includes a proximal portion defined by a plurality of flexible legs.

In certain embodiments, the first engagement structure is formed on the proximal portion of the plurality of flexible legs.

In embodiments, the first engagement structure includes an annular channel.

In some embodiments, the proximal portion of each of the plurality of flexible legs is tapered towards a longitudinal axis of the knife carrier in the proximal direction.

In certain embodiments, the second engagement structure includes and annular wall configured to be received within the annular channel of the first engagement structure.

In embodiments, the annular wall includes a tapered proximal surface that defines a back angle Ω with the longitudinal axis of the knife carrier. The tapered proximal surface of the annular wall is configured to urge the first engagement structure from the first position towards the second position.

In some embodiments, the back angle Ω is between 15 degrees and 75 degrees.

In certain embodiments, the back angle Ω is between 30 degrees and 60 degrees.

In embodiments, the annular channel of the first engagement structure is defined by distal and proximal walls and the proximal wall is orthogonal in relation to the longitudinal axis of the knife carrier.

In some embodiments, the handle assembly is an electrically powered handle assembly.

In certain embodiments, the reload assembly is releasably coupled to the elongate body.

In embodiments, the reload member is integrally formed with the inner housing portion of the housing.

In some embodiments, the pusher assembly includes an annular pusher and a staple pushing member.

In certain embodiments, the annular pusher is positioned to abut a proximal end of the staple pushing member.

In embodiments, the stapling device includes a handle assembly and the elongate body extends distally from the handle assembly.

BRIEF DESCRIPTION OF THE DRAWINGS

Various embodiments of the presently disclosed surgical stapling device including a releasable knife carrier are described herein below with reference to the drawings, wherein:

FIG. 6 is a cross-sectional view taken along section line 6-6 of FIG. 2 illustrating a distal end of the surgical stapling device in a pre-fired state;

FIG. 6A is an enlarged view of the indicated area of detail shown in FIG. 6 illustrating the knife carrier and the knife carrier pusher in an engaged state;

FIG. 6B is a view of the indicated area of detail shown in FIG. 6A illustrating the knife carrier and the knife carrier pusher as the knife carrier is moved into engagement with the knife carrier pusher;

DETAILED DESCRIPTION OF EMBODIMENTS

Figure 1:
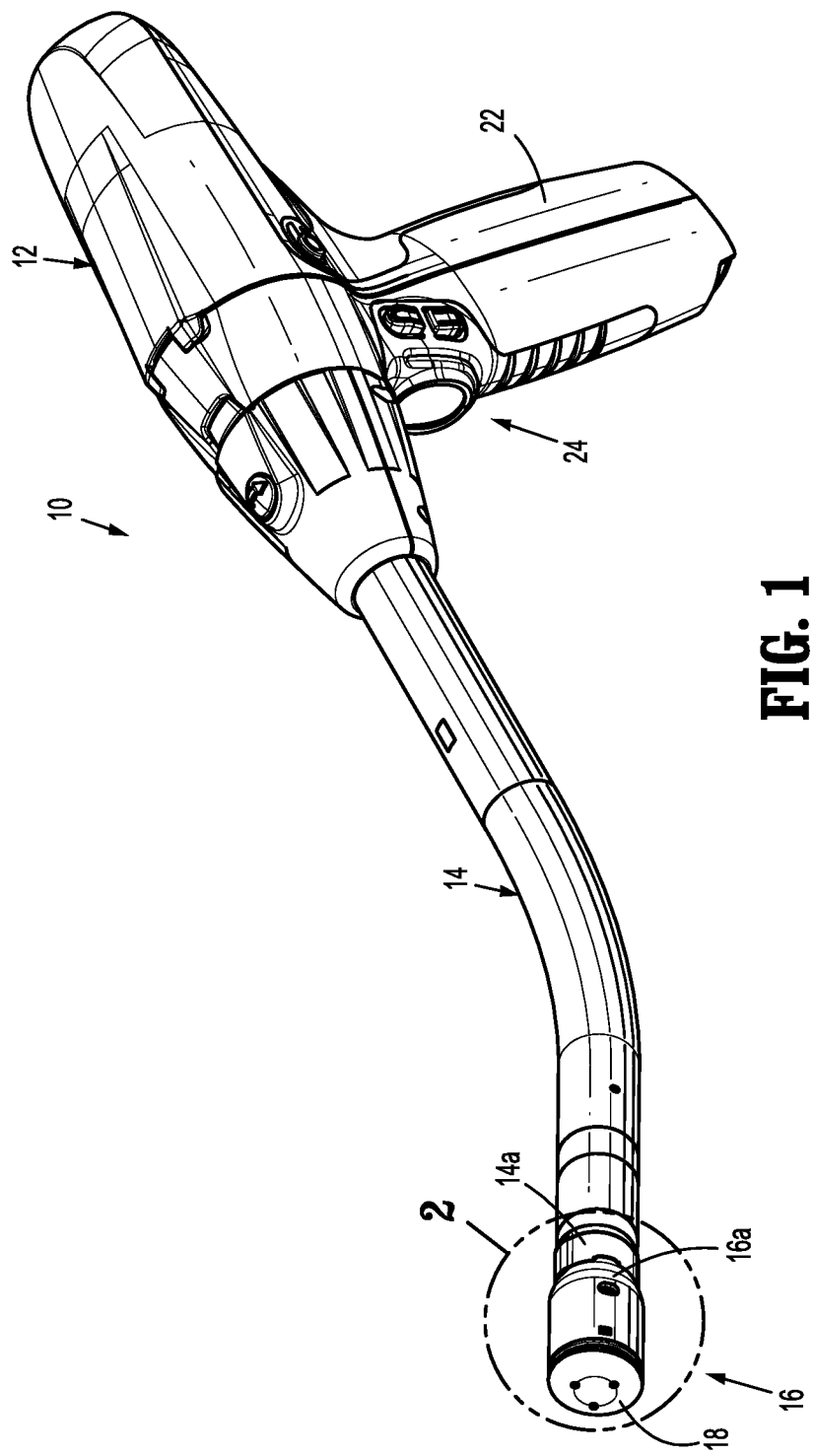
FIG. 1 is a side perspective view of one exemplary embodiment of the presently disclosed surgical stapling device including a reload assembly and an anvil assembly with the anvil assembly in an approximated position.

The presently disclosed circular stapling device will now be described in detail with reference to the drawings in which like reference numerals designate identical or corresponding elements in each of the several views. In this description, the term "proximal" is used generally to refer to that portion of the stapling device that is closer to a clinician, while the term "distal" is used generally to refer to that portion of the stapling device that is farther from the clinician. In addition, the term "clinician" is used generally to refer to medical personnel including doctors, surgeons, nurses, and support personnel.

The presently disclosed circular stapling device includes a shell or reload assembly that is supported on a distal end of an elongate shaft of the stapling device. The reload assembly includes a housing having an inner housing portion defining a through bore, a staple cartridge that supports a plurality of annular rows of staples, a staple pusher assembly, a knife carrier, and an annular knife supported on the knife carrier. The elongate body includes a pusher drive member and a knife carrier pusher. The knife carrier includes resilient legs that are movable from a first position engaged with the knife carrier pusher to couple the knife carrier to the knife carrier pusher to a second position disengaged from the knife carrier pusher. A reload insert is supported within a through bore of an inner housing portion of the reload assembly and includes a first portion configured to retain the resilient legs in the first position and a second portion configured to accommodate movement of the resilient legs from the first position to the second position.

In a pre-fired state of the stapling device, the pusher drive member and the pusher are positioned to retain the resilient legs of the knife carrier in engagement with the knife carrier pusher. After the stapling device is fired as the knife carrier and knife are being retracted into the housing of the reload assembly, the reload insert is positioned and configured to prevent inward movement of the resilient legs of the knife carrier until the knife has been fully retracted into the housing. When the knife has been fully retracted into the housing of the reload assembly, the tapered portion of the reload insert is positioned and configured to accommodate inward movement of the resilient legs of the knife carrier to facilitate disengagement of the knife carrier from the knife carrier pusher as described in detail below. The presently disclosed reload insert minimizes the likelihood of premature separation of the knife carrier from the knife carrier pusher while reducing the force required to effect separation of the knife carrier from the knife carrier pusher after the knife has been fully retracted into the housing.

Figure 2:
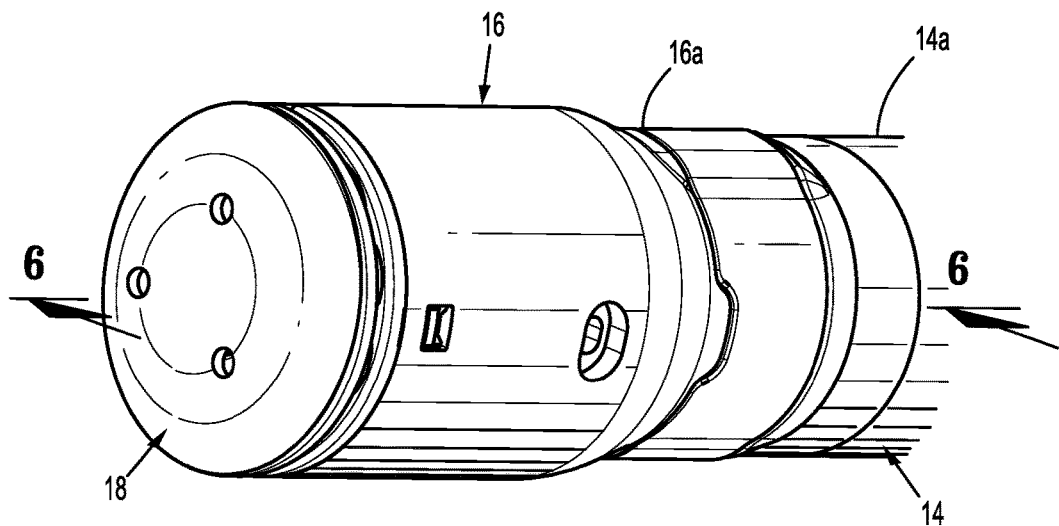
FIG. 2 is an enlarged view of the indicated area of detail shown in FIG. 1.

FIGS. 1 and 2 illustrate an exemplary embodiment of the presently disclosed surgical stapling device 10. The stapling device 10 includes a handle assembly 12, an elongate body or adaptor assembly 14, a reload assembly 16, and an anvil assembly 18 supported for movement in relation to the reload assembly 16 between spaced and approximated positions as is known in the art. The reload assembly 16 includes a proximal end 16a that is releasably coupled to a distal end 14a of the elongate body 14. The handle assembly 12 includes a stationary grip 22, and actuation buttons 24 for controlling operation of the various functions of the stapling device 10 including approximation of the reload and anvil assemblies 16, 18, firing of staples (not shown) from the reload 16, and cutting of tissue. Although the surgical stapling device 10 is illustrated as an electrically powered stapling device including an electrically powered handle assembly 12 and an elongate body 14 in the form of an adaptor assembly that translates power from the handle assembly 12 to the reload and anvil assemblies 16, 18, it is envisioned that the present disclosure could also be incorporated into a manually powered stapling device. Examples of electrically powered stapling devices can be found in U.S. Pat. No. 9,023,014 ("the '014 patent"), and U.S. Pat. No. 9,055,943 ("the '943 patent) which are incorporated herein by reference in their entirety. Alternately, the device 10 can be configured for attachment to a robotic system and need not include a handle assembly.

Figure 2A:
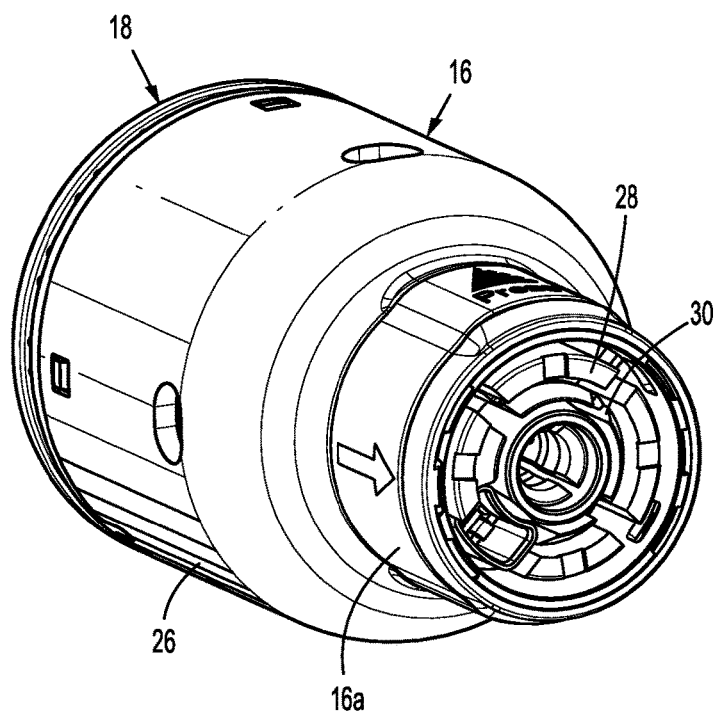
FIG. 2A is a perspective view from a proximal end of the reload assembly and anvil assembly of the surgical stapling device shown in FIG. 1.
Figure 3:
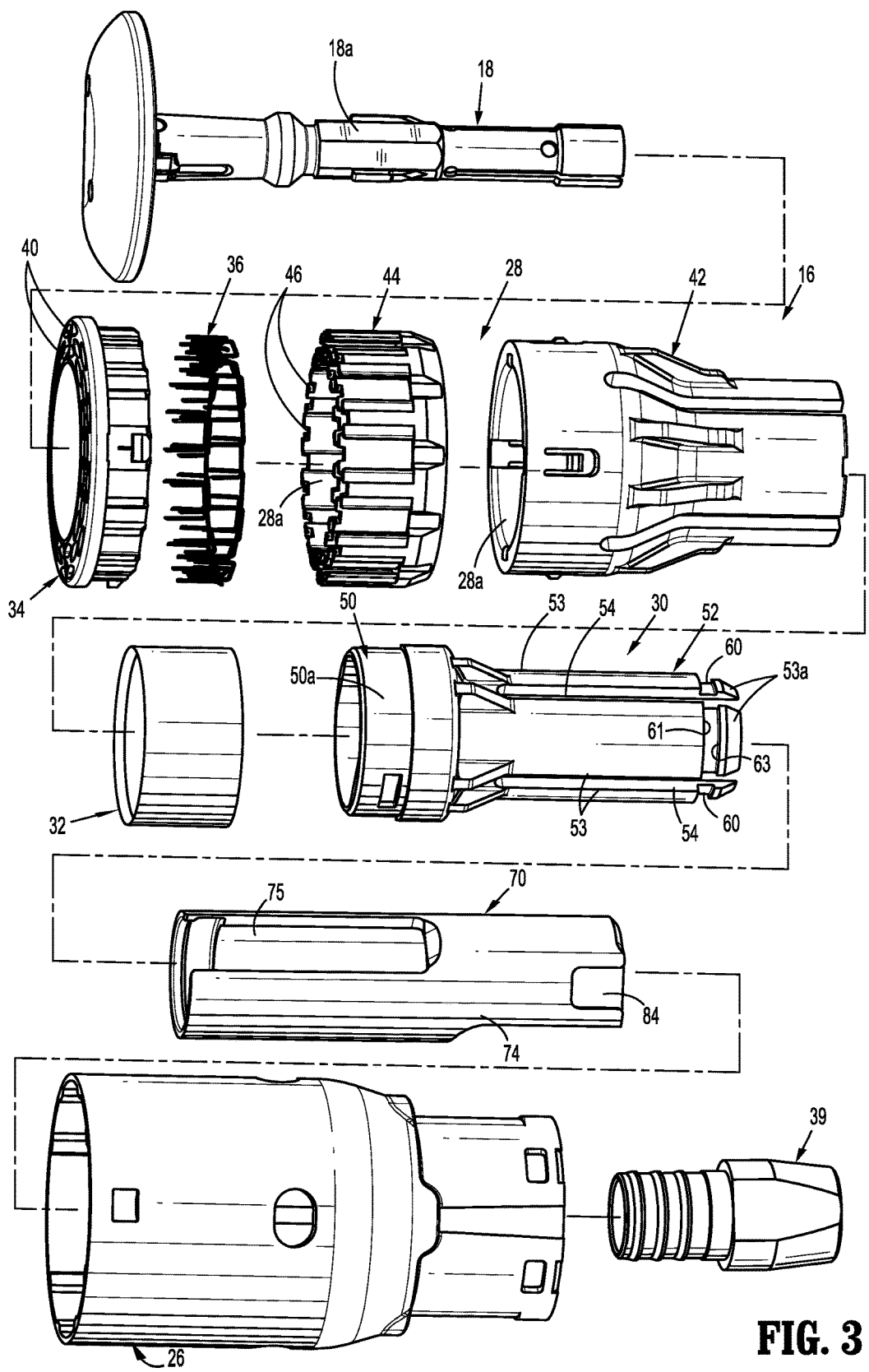
FIG. 3 is a side perspective view with parts separated of a distal portion of the presently disclosed surgical stapling device including the reload assembly and anvil assembly shown in FIG. 2A.

Referring to FIGS. 2A-3, the reload assembly 16 includes a housing 26, a pusher assembly 28, a knife carrier 30, an annular knife 32 supported on the knife carrier 30, a staple cartridge 34, staples 36 supported within the staple cartridge 34, and a reload insert 39. The staple cartridge 34 defines annular rows of staple pockets 40 (FIG. 3). Each of the staple pockets 40 supports one of the staples 36. The pusher assembly 28 includes an annular pusher 42 and a staple pushing member 44 that together define a longitudinal through bore 28a. The pusher 42 has a distal end that engages a proximal end of the staple pushing member 44 such that distal movement of the pusher 42 within the housing 26 effects distal movement of the staple pushing member 44 within the housing 26. The staple pushing member 44 of the reload 16 has a plurality of fingers 46.

Each of the plurality of fingers 46 is received within a respective one of the staple pockets 40 of the staple cartridge 34 and is movable through the staple pocket 40 to eject the staple 36 from the staple pocket 40 when the staple pushing member 44 is moved distally within the housing 26 from a retracted position to an advanced position.

Figure 4:
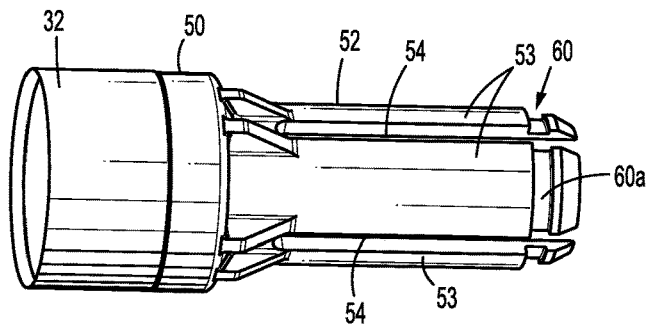
FIG. 4 is a side perspective view of a knife carrier of the reload assembly shown in FIG. 3.

The reload insert 39 is fixedly secured to an inner housing portion 26*a* (FIG. 6) of the housing 26 and defines a through bore 41. The anvil assembly 18 includes an anvil shaft 18*a* that is movable within the through bore 41 as the anvil assembly 18 moves between the spaced and approximated positions in relation to the staple cartridge 34. Referring also to FIG. 4, the knife carrier 30 is movably supported within the through bore 28*a* of the pusher assembly 28 and includes a substantially cylindrical distal portion 50 and a substantially cylindrical smaller diameter proximal portion 52. The smaller diameter proximal portion 52 is defined by a plurality of spaced resilient legs 53 that define slots 54 therebetween. The slots 54 receive projections (not shown) defined within the pusher 42 to guide movement of the knife carrier 30 from a retracted position to an advanced position within the pusher assembly 28. The longitudinal slots 54 also facilitate inward flexing of the resilient legs 53 of the knife carrier 30 to facilitate engagement and disengagement of the knife carrier 30 and the knife carrier pusher 70. The knife 32 is secured about the distal portion 50 of the knife carrier 30 such as by crimping. Alternately, other fastening techniques can be used to secure the knife 32 to the knife carrier 30. In embodiments, a distal-most portion 50*a* of the distal portion 50 of the knife carrier 30 is recessed to receive the annular knife 32.

Figure 5B:
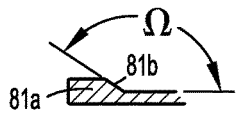
FIG. 5B is a cross-sectional view taken along section line 5B-5B of FIG. 5.
Figure 5:
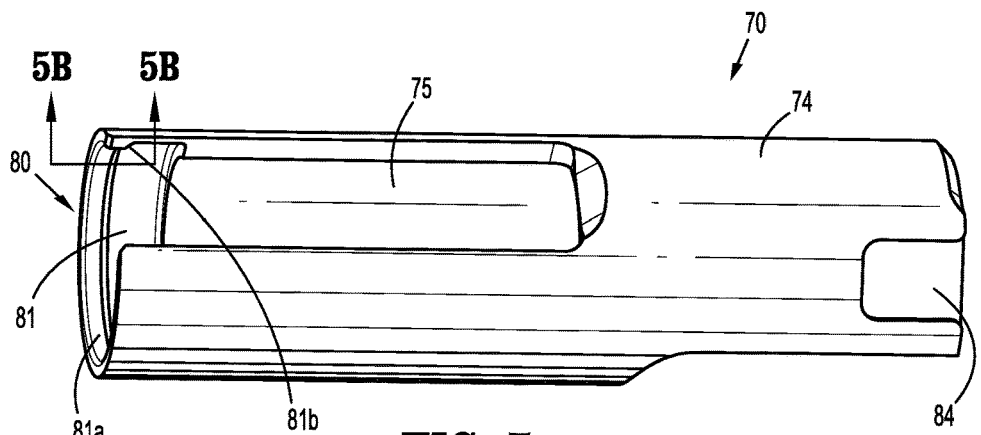
FIG. 5 is a side perspective view of a knife carrier pusher of the reload assembly shown in FIG. 3.

Referring to FIGS. 3 and 4, each of the resilient legs 53 of the knife carrier 30 defines a longitudinal axis and includes first engagement structure 60 that is configured to engage a distal end of a knife carrier pusher 70 (FIG. 5) of the elongate body 14 as described in detail below to releasably couple the knife carrier 30 to the knife carrier pusher 70 (FIG. 5). In embodiments, the first engagement structure 60 includes an annular channel 60*a* that is configured to receive second engagement structure 80 (FIG. 5) formed on a distal end of the knife carrier pusher 70 as described in further detail below. The annular channel 60*a* of the first engagement structure 60 is defined by distal and proximal walls 61, 63, wherein the proximal wall 63 is orthogonal in relation to a longitudinal axis of the knife carrier 30. In embodiments, a proximal end 53*a* of each resilient leg 53 of the knife carrier 30 is tapered inwardly towards the longitudinal axis in a proximal direction. The tapered proximal end 53*a* and the longitudinal slots 54 of the knife carrier 30 facilitate attachment of the knife carrier 30 to the distal end of the knife carrier pusher 70 as described in detail below.

Referring also to FIG. 5, the knife carrier pusher 70 includes a substantially cylindrical body 74 having a cutout 75 that extends from a central portion of the body 74 to the distal end of the body 74. In embodiments, the second engagement structure 80 includes an annular protrusion 81*a* formed along an inner wall 81 at the distal end of the body 74. The annular protrusion 81*a* has a tapered proximal surface 81*b* (FIG. 5B) defining a back angle Ω with a longitudinal axis of the knife carrier pusher 70 and knife carrier 30. In embodiments, the back angle Ω is between about 15 degrees and about 75 degrees. In other embodiments, the back angle Ω is between about 30 degrees and about 60 degrees.

The cylindrical body 74 of the knife carrier pusher 70 defines recesses 84 that are configured to engage a drive member (not shown) supported within the elongate body 14. The drive member is secured to the proximal end of the knife carrier pusher 70 and is operable to advance and retract the knife carrier pusher 70 within the housing 26 of the reload assembly 16 as known in the art. U.S. Publication No. 2016/0106406 ("the '406 Publication") which was filed on Oct. 6, 2015 discloses such an elongate body or adaptor and is incorporated herein in its entirety by reference.

Figure 5A:
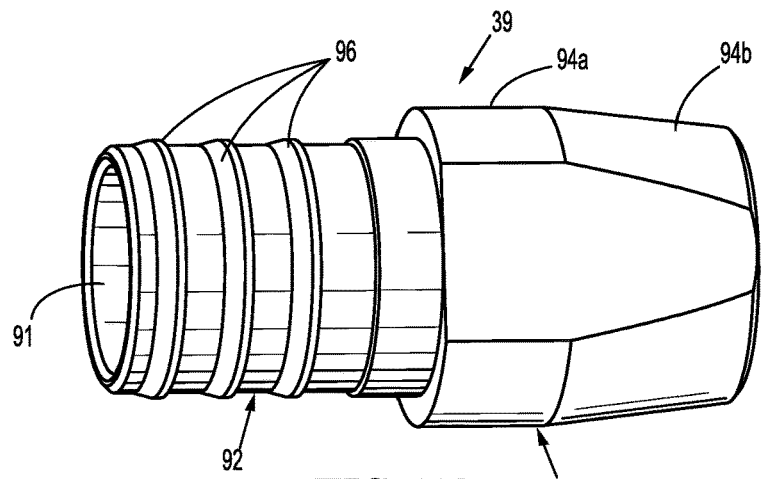
FIG. 5A is a side perspective view of a tapered shell insert of the reload assembly shown in FIG. 3.

Referring also to FIGS. 5A and 6, the reload insert 39 defines a through bore 91 and includes a distal portion 92 and a proximal portion 94. The through bore 91 is dimensioned to receive the anvil shaft 18*a* of the anvil assembly 18 when the anvil shaft 18*a* is connected to an anvil retainer (not shown) of the stapling device 10 and the anvil assembly 18 is moved between the spaced and approximated positions in relation to the staple cartridge 34. The distal portion 92 of the reload insert 39 is dimensioned to be fixedly received within the through bore 41 defined by the inner housing portion 26*a* (FIG. 6) of the housing 26. In embodiments, the distal portion 92 is substantially cylindrical and includes a series of spaced rings 96. When the distal portion 92 of the reload insert 39 is positioned within the through bore 26*a*, the spaced rings 96 engage an inner wall of the inner housing portion 26*a* of the housing 26 to fixedly retain the reload insert 39 within the housing 26.

The proximal portion 94 of the reload insert 39 has a first cylindrical portion 94*a* and a second frusto-conical or tapered portion 94*b* that tapers inwardly from the cylindrical portion 94*a* towards a longitudinal axis of the reload insert 39 in a proximal direction. The cylindrical portion 94*a* of the reload insert 39 is configured to prevent inward movement of the resilient legs 53 of the knife carrier 30 to retain the resilient legs 53 in an engaged state with the knife carrier pusher 70 when the knife carrier 30 is positioned distally of its retracted position and the distal end of the knife 32 is positioned externally of the housing 26. When the knife carrier pusher 70 is moved to a fully retracted position such that the knife 32 is withdrawn into the housing 26 of the reload assembly 16, the tapered portion 94*b* of the reload insert 39 is positioned to accommodate inward pivotal movement of the resilient legs 53 of the knife carrier 30 to facilitate engagement and disengagement of the knife carrier 30 and the knife carrier pusher 70.

Although illustrated as a separate component, it is envisioned that the insert 39 can be integrally formed with the inner housing portion 26*a* of the reload assembly 16.

FIGS. 6 and 6A illustrate the stapling device 10 in a pre-fired state. In the pre-fired state, the pusher assembly 28 and the knife carrier 30 of the reload 16, and the knife carrier pusher 70 and the pusher drive member 90 of the elongate body 14 are in retracted positions. In their retracted positions, the pusher assembly 28 and the pusher drive member 90 extend about an interface 106 between the first engagement structure 60 on the proximal end of the resilient legs 53 of the knife carrier 30 and the second engagement structure 80 positioned on the distal end of the knife carrier pusher 70. In this state, the knife carrier 30 and the knife carrier pusher 70 are engaged.

When the knife carrier pusher 70 is in its retracted position, the reload insert 39 is positioned within the knife carrier 30 such that the tapered portion 94*b* of the reload insert 39 is positioned adjacent the interface 106 between the first engagement structure 60 on the proximal end of the knife carrier 30 and the second engagement structure 80 on the knife carrier pusher 70. Positioning the interface 106 for the first and second engagement structures 60, 80 adjacent the tapered portion 94*b* of the reload insert 39 in the retracted position allows the reload 16 to be secured to the elongate body 14 prior to actuation of the stapling device 10. More specifically, as shown in FIG. 6B, when the reload 16 is inserted into the distal end of the elongate body 14 in the direction indicated by arrow "A" to attach the reload 16 to the elongate body 14, the tapered proximal ends 52a of the resilient legs 53 engage the a flat distal face 108 of the knife carrier pusher 70. When this occurs, the tapered proximal ends 52a of the resilient legs 53 are cammed inwardly to flex the resilient legs 53 inwardly and allow the first engagement structure 60 to move into engagement with the second engagement structure 80. The tapered portion 94b of the reload insert 39 provides space to accommodate the inwardly flexing legs 53 and thereby facilitate engagement of the first and second engagement structures 60, 80.

Figure 6C:
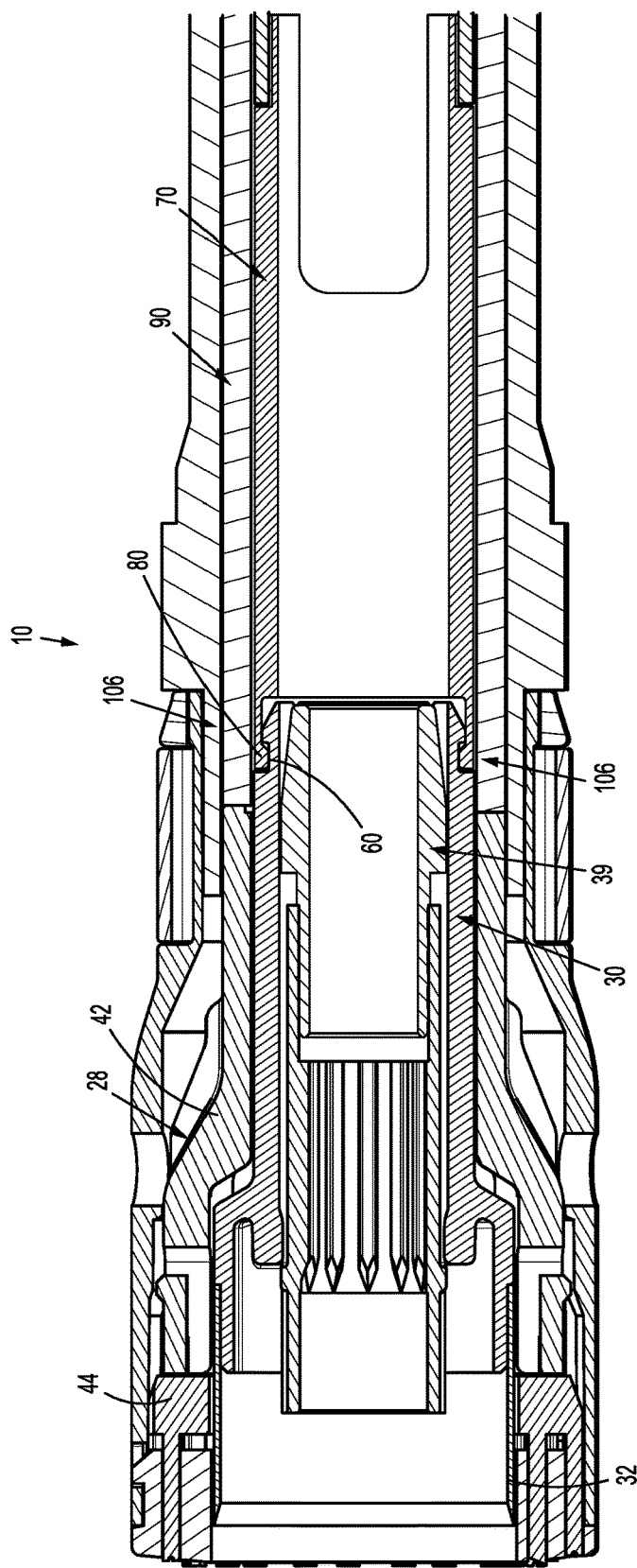
FIG. 6C is a side cross-sectional view of the distal end of the surgical stapling device shown in FIG. 6 in a post-fired state with the knife carrier and knife carrier pusher in a retracted position.

FIG. 6C illustrates the stapling device 10 in a post-fired state with the pusher assembly 28 and the pusher drive member 90 in advanced positions and the knife carrier 30, the knife 32, and the knife carrier pusher 70 in retracted positions. In this state, the interface 106 between the first and second engagement structures 60, 80 of the knife carrier 30 and the knife carrier pusher 70, respectively, is positioned within the pusher drive member 90 and the staples 36 (FIG. 3) have been ejected from the staple cartridge 34.

Figure 7:
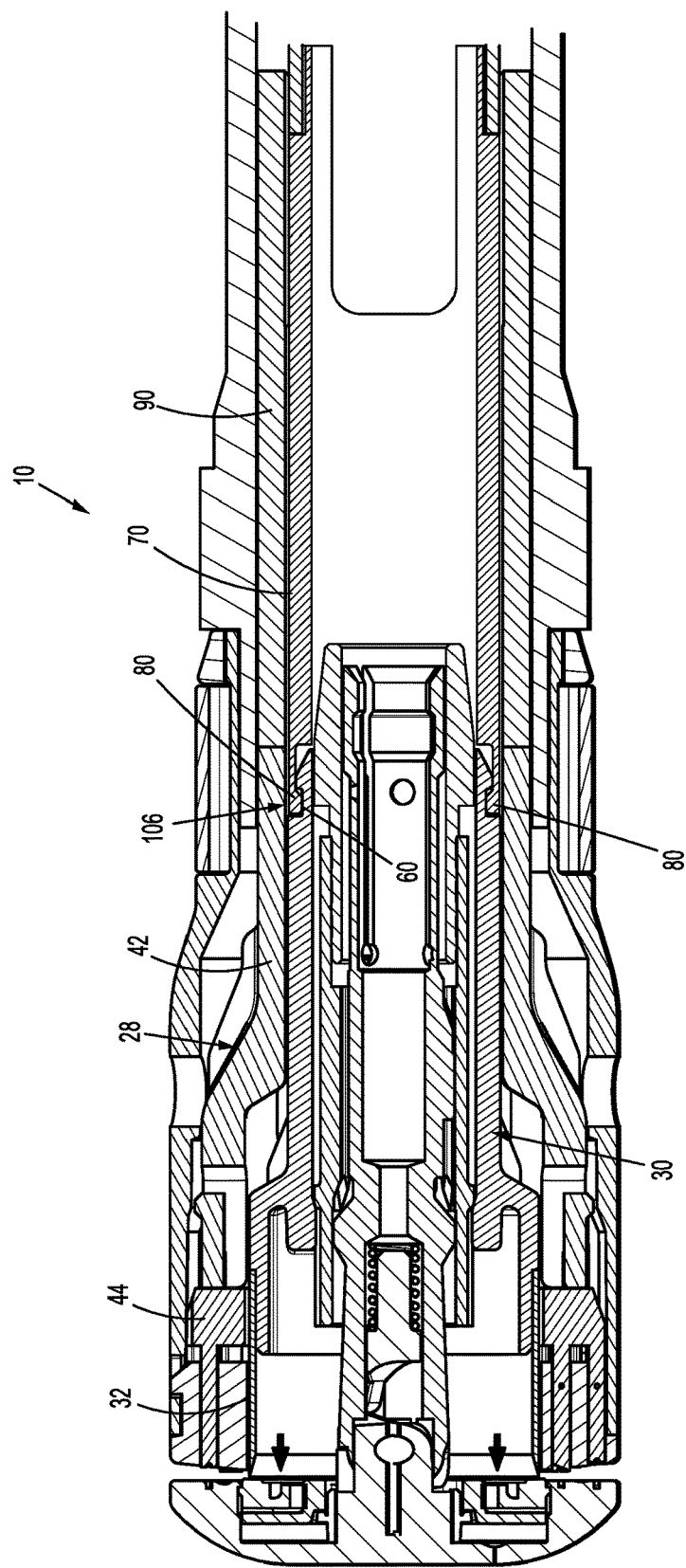
FIG. 7 is a side cross-sectional view of the distal end of the surgical stapling device shown in FIG. 6C in a post-fired state with the knife carrier and knife carrier pusher in an advanced position.

FIG. 7 illustrates the stapling device 10 in a post-fired state after the knife carrier pusher 70 and the knife 32 have been advanced. In this state, the pusher assembly 28, the pusher drive member 90, the knife carrier 30 and the knife carrier pusher 70 are in advanced positions, and the interface 106 between the first and second engagement structures 60, 80 of the knife carrier 30 and the knife carrier pusher 70, respectively, is positioned within the pusher drive member 90 distally of the tapered portion 94b of the reload insert 39 adjacent cylindrical portion 94a of the reload insert 39. Thus, inward movement of the resilient legs 53 of the knife carrier 30 is prevented and the knife carrier 30 and the knife carrier pusher 70 remain in engagement.

Figure 8:
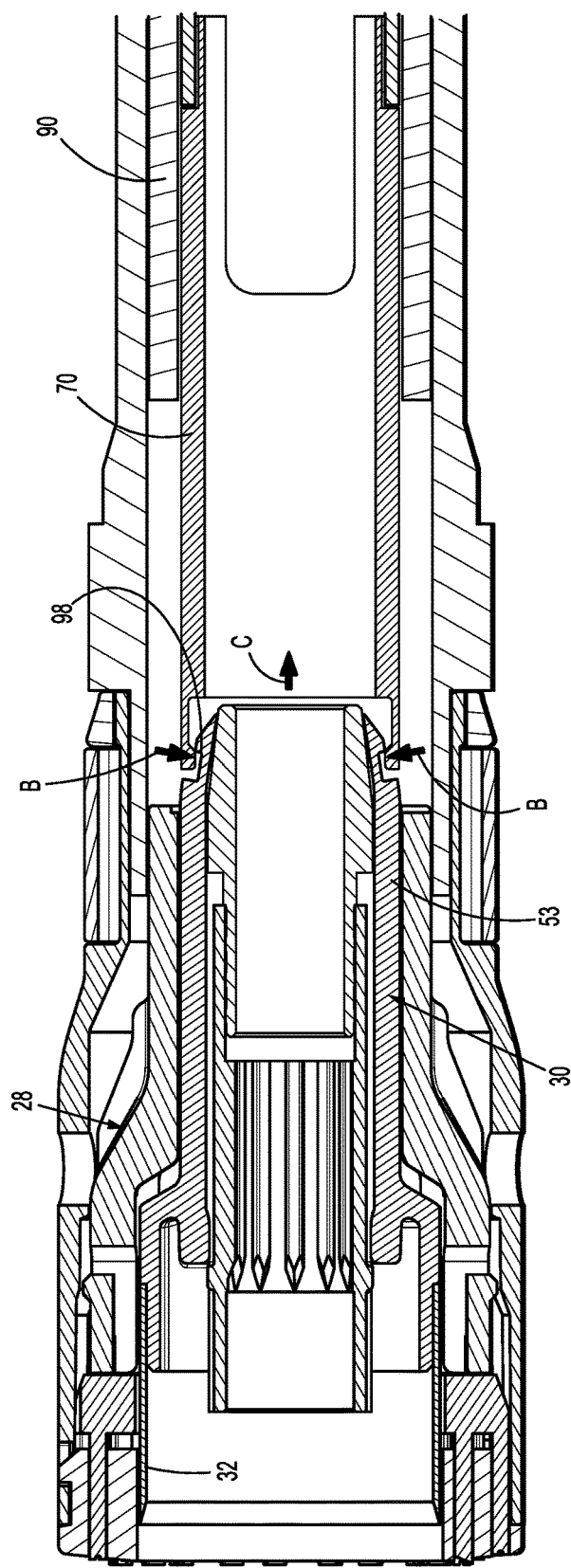
FIG. 8 is a side cross-sectional view of the distal end of the surgical stapling device in a post-fired state with the knife carrier and the drive member in a retracted position, and the knife carrier pusher moving towards its retracted position to facilitate separation of the knife carrier and the knife carrier pusher.

Referring to FIG. 8, after the staples 36 (FIG. 3) have been fired and tissue has been cut, the knife carrier pusher 70 is retracted to retract the knife carrier 30. As the knife carrier pusher 70 is retracted, the tapered proximal surface 81b defining the back angle Ω (FIG. 5B) on the annular protrusion 81a of the second engagement structure 80 of the knife carrier pusher 70 is pulled against a proximal wall 98 defining the annular channel 60a of the first engagement structure 60. This force of proximal surface 81b on proximal wall 98 urges the flexible legs 53 of the first engagement structure 60 inwardly (FIG. 6A). However, the cylindrical portion 94a of the reload insert 39 is positioned to prevent inward movement of the flexible legs 53 of the knife carrier 30 until the knife 32 is fully retracted into the housing 26 and the flexible legs 53 are aligned with the tapered portion 94b of the reload insert 39. When the flexible legs 53 are aligned with the tapered portion 94b of the reload insert 39, the force of the proximal surface 81b of the second engagement structure 80 on proximal wall 98 of the first engagement structure 60 urges the flexible legs 53 of the first engagement structure 60 inwardly in the direction indicated by arrows "B" to effect separation of the knife carrier pusher 70 from the knife carrier 30. The tapered reload insert 39 functions to control the timing of separation between the knife carrier 30 from the knife carrier pusher 70 to minimize the likelihood of premature separation of the knife carrier 30 from the knife carrier pusher 70 while minimizing the force required to effect separation of the knife carrier 30 and the knife carrier pusher 70.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an elongate body defining a longitudinal axis and having a proximal portion and a distal portion, the elongate body including a pusher drive member and a knife carrier pusher, the knife carrier pusher movable independently of the pusher drive member;
a reload assembly including a housing including an inner housing portion defining a housing through bore, a staple cartridge supporting a plurality of staples, a pusher assembly movably supported within the housing between a retracted position and an advanced position to eject the plurality of staples from the staple cartridge, and a knife carrier supporting a knife, the knife carrier including first engagement structure;
wherein the knife carrier pusher includes a second engagement structure that is configured to releasably engage the first engagement structure of the knife carrier to couple the knife carrier pusher to the knife carrier, the first engagement structure being movable from a first position engaged with the second engagement structure to a second position disengaged from the second engagement structure; and
a reload member supported on the housing, the reload member having a first portion configured to prevent movement of the first engagement structure from the first position to the second position and a second portion configured to accommodate movement of the first engagement structure from the first position to the second position.

2. The surgical stapling device of claim 1, wherein the reload member includes an insert secured to the inner housing portion.

3. The surgical stapling device of claim 2, wherein the insert defines a through bore and includes a distal portion configured to be received within the housing through bore and a proximal portion that defines the first and second portions of the reload member.

4. The surgical stapling device of claim 3, wherein the first portion of the reload member is cylindrical and the second portion of the reload member tapers from the first portion towards a longitudinal axis of the reload member in a proximal direction.

5. The surgical stapling device of claim 1, wherein the knife carrier is movably positioned within a through bore defined by the pusher assembly.

6. The surgical stapling device of claim 1, wherein the knife carrier includes a proximal portion defined by a plurality of flexible legs.

7. The surgical stapling device of claim 6, wherein the first engagement structure is formed on the proximal portion of the plurality of flexible legs.

8. The surgical stapling device of claim 7, wherein the first engagement structure includes an annular channel.

9. The surgical stapling device of claim 8, wherein the proximal portion of each of the plurality of flexible legs is tapered towards a longitudinal axis of the knife carrier in the proximal direction.

10. The surgical stapling device of claim 8, wherein the second engagement structure includes an annular wall configured to be received within the annular channel of the first engagement structure.

11. The surgical stapling device of claim 10, wherein the annular wall includes a tapered proximal surface that defines a back angle $\Omega$ with the longitudinal axis of the knife carrier, the tapered proximal surface of the annular wall being configured to urge the first engagement structure from the first position towards the second position.

12. The surgical stapling device of claim 11, wherein the back angle $\Omega$ is between 15 degrees and 75 degrees.

13. The surgical stapling device of claim 12, wherein the back angle $\Omega$ is between 30 degrees and 60 degrees.

14. The surgical stapling device of claim 12, wherein the annular channel of the first engagement structure is defined by distal and proximal walls, the proximal wall being orthogonal in relation to the longitudinal axis of the knife carrier.

15. The surgical stapling device of claim 1, further including a handle assembly, wherein the handle assembly is an electrically powered handle assembly.

16. The surgical stapling device of claim 1, wherein the reload assembly is releasably coupled to the elongate body.

17. The surgical stapling device of claim 1, wherein the reload member is integrally formed with the inner housing portion of the housing.

18. The surgical stapling device of claim 1, wherein the pusher assembly includes an annular pusher and a staple pushing member.

19. The surgical stapling device of claim 18, wherein the annular pusher is positioned to abut a proximal end of the staple pushing member.

20. The surgical stapling device of claim 1, further including a handle assembly, the elongate body extending distally from the handle assembly.

* * * * *